United States Patent [19]

Wakatsuka et al.

[11] Patent Number: 4,783,480
[45] Date of Patent: Nov. 8, 1988

[54] 6-KETO-PROSTAGLANDIN $E_1$ DERIVATIVES

[75] Inventors: Hirohisa Wakatsuka, Takatsuki; Tadao Okegawa, Yawata; Yoshinobu Arai, Osaka, all of Japan

[73] Assignee: Ono Pharmaceutical Co., Ltd., Osaka, Japan

[21] Appl. No.: 7,657

[22] Filed: Jan. 28, 1987

[30] Foreign Application Priority Data

Jan. 30, 1986 [JP] Japan .................................. 61-16722

[51] Int. Cl.$^4$ .................. C07C 177/00; A01K 31/557
[52] U.S. Cl. .................................. 514/423; 514/530; 514/570; 514/571; 514/573; 514/613; 514/621; 548/533; 549/415; 549/473; 560/39; 560/40; 560/118; 560/121; 562/444; 562/445; 562/500; 562/503; 564/169; 564/189
[58] Field of Search ................... 560/121, 118, 39, 40; 564/169, 189; 562/444, 445, 500, 503; 548/533; 514/530, 423, 573, 590, 571, 621, 613; 549/415, 43

[56] References Cited

PUBLICATIONS

Chemical Abstract, vol. 85, No. 11, Sep. 13th 1976, p. 512.
Chemical Abstract, vol. 84, No. 7, Feb. 16th 1976; p. 436.
Chemical Abstract, vol. 83, No. 15, Oct. 13th 1975, p. 471.

Primary Examiner—Robert Gerstl
Attorney, Agent, or Firm—Stevens, Davis, Miller & Mosher

[57] ABSTRACT

A 6-keto-prostaglandin $E_1$ derivative of the formula:

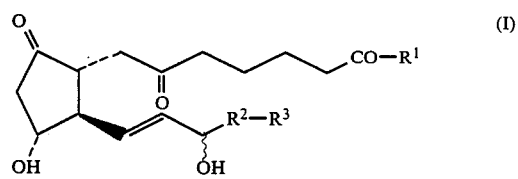

(wherein $R^1$ represents an amino acid or amino alcohol residue, $R^2$ represents a single bond or an alkylene group of from 1 to 4 carbon atoms, $R^3$ represents (i) an alkyl group of from 1 to 8 carbon atoms, (ii) a cycloalkyl group of from 4 to 7 carbon atoms, which may be unsubstituted or substituted by at least one alkyl group of from 1 to 8 carbon atoms or (iii) a phenyl or phenoxy group, which may be unsubstituted or substituted by chlorine, trifluoromethyl or alkyl of from 1 to 3 carbon atoms, provided that when $R^2$ represents a single bond $R^3$ does not represent phenoxy)
cyclodextrin clathrates thereof and non-toxic salts thereof possess selective cytoprotective activity.

10 Claims, No Drawings

6-KETO-PROSTAGLANDIN $E_1$ DERIVATIVES

This invention relates to novel 6-keto-prostaglandin $E_1$ derivatives which possess cytoprotective activity, processes for their preparation and pharmaceutical compositions containing them.

A prostaglandin (abbreviated to PG hereinafter) is a derivative of prostanoic acid which has the formula:

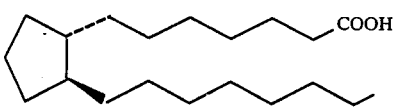
(A)

and various types of prostaglandins are known.

In the formulae in this specification, in accordance with generally accepted rules of nomenclature, the broken line (----), the thickened line (——) and the wavy line (∼∼∼) indicate attachment in α-configuration, β-configuration, or a mixture thereof, respectively.

PGs are generally known to possess pharamacological properties, for example, they have hypotensive activity, diuretic activity, bronchodilating activity and antinidatory activity; they inhibit blood platelet aggregation, gastric acid secretion, gastro-intestinal ulcers and the release of fatty acid. The properties of PGs are indicative of therapeutic utility.

However, if a PG is to be used in therapy it is generally desirable to use only one pharmacological property: other pharmacological properties then cause undesired side effects. The principal object of research into therapeutically useful PGs has therefore been to produce compounds which exert a selective action, ie. in which there is a substantial difference between the dose required to produce the desired effect and that required to cause undesired side effects.

It is known from British Pat. No. 2,006,753 that 6-keto-$PGE_1$ derivatives of the general formula:

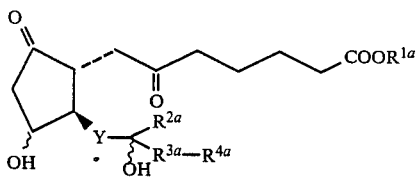
(B)

[wherein Y represents a trans-vinylene group

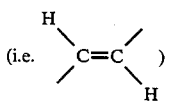

or ethylene group (i.e. —$CH_2CH_2$—), $R^{1a}$ represents a hydrogen atom or a straight or branched chain alkyl group of from 1 to 12 carbon atoms, $R^{2a}$ represents a hydrogen atom or a methyl group or ethyl group, $R^{3a}$ represents a single bond or a straight or branched chain alkylene group of from 1 to 4 carbon atoms, $R^{4a}$ represents a hydrogen atom, a straight or branched chain alkyl group of from 1 to 8 carbon atoms, a cycloalkyl group of from 4 to 7 carbon atoms unsubstituted or substituted by at least one straight or branched chain alkyl group of from 1 to 8 carbon atoms or a phenyl or phenoxy group unsubstituted or substituted by at least one chlorine atom, trifluoromethyl group or alkyl group of from 1 to 3 carbon atoms, and the wavy lines (∼∼∼) on the carbon atoms in the 11- and 15-positions represent α- or β-configuration (i.e. S- or R-configuration) or a mixture thereof] and cyclodextrin clathrates thereof and, when $R^{1a}$ represents a hydrogen atom, non-toxic salts thereof possess pharmacological activity.

It is also known from European Patent Publication No. 0,122,019 that the prostaglandin analogues of the formula:

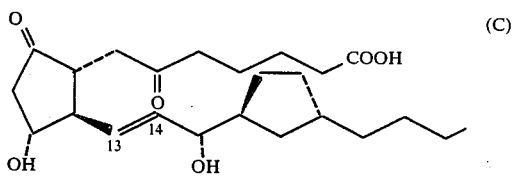
(C)

[wherein the symbol —— represents β-configuration, the dotted line --- represents α-configuration and the double bond between $C_{13}$ and $C_{14}$ represents trans-configuration] and cyclodextrin clathrates thereof possess cytoprotective activity.

However, the use of such 6-keto-$PGE_1$ derivatives as pharmaceuticals, specifically in the treatment of cytodamage, is precluded, even when such compounds exert a strong cytoprotective action, by the incidence of side effects.

Prostaglandin derivatives in which an amino acid moiety is incorporated into the carboxylic acid grouping of $PGF_2$ or $PGE_2$ are known from Japanese Patent Kokai Nos. 50-13363, 50-71650 and 50-140422, which describe, respectively, compounds of the general formula:

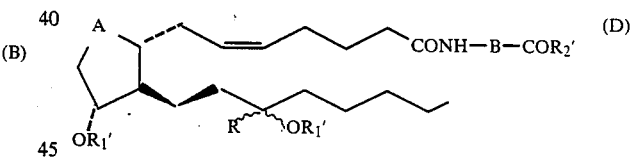
(D)

[wherein R represent a hydrogen atom or a lower alkyl group, $R_1'$ represent a hydrogen atom or a protecting group, $R_2'$ represents a hydroxy group, an amino group or a lower alkoxy group, A represents

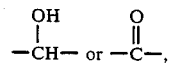

and the grouping NH—B—$COR_2'$ represents an amino acid or peptide moiety];

compounds of the general formula:

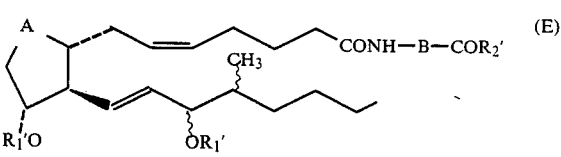
(E)

wherein A, B, $R_1'$ and $R_2'$ are as hereinbefore defined; and compounds of the general formula:

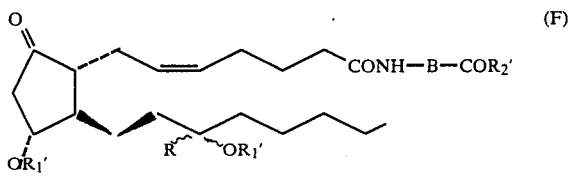

(F)

wherein R, $R_1'$, $R_2'$ and B are as hereinbefore defined.

These compounds are described as possessing superior bioactivities to $PGF_{2\alpha}$ or $PGE_2$; there is no reference to any reduction in the incidence of side effects.

As a result of research and experimentation it has been discovered that when the carboxy group of certain 6-keto-$PGE_1$ derivatives is replaced by an amino acid-containing moiety as hereinafter defined the novel compounds produced surprisingly possess a useful level of cytoprotective activity associated with a low level of side effects.

The present invention accordingly provides the novel 6-keto-prostaglandin $E_1$ derivatives of the general formula:

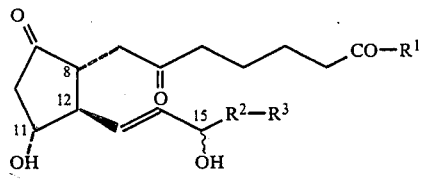

(I)

(wherein $R^1$ represents an amino acid or amino alcohol residue attached to the CO-group by its amino group, $R^2$ represents a single bond or an alkylene group of from 1 to 4 carbon atoms, $R^3$ represents (i) an alkyl group of from 1 to 8 carbon atoms, (ii) a cycloalkyl group of from 4 to 7 carbon atoms, which is unsubstituted or substituted by at least one alkyl group of from 1 to 8 carbon atoms or (iii) a phenyl or phenoxy group, which is unsubstituted or substituted by at least one chlorine atom, trifluoromethyl group or alkyl group of from 1 to 3 carbon atoms, with the proviso that when $R^2$ represents a single bond $R^3$ does not represent a phenoxy group) or a cyclodextrin clathrate thereof or a salt, preferably a non-toxic salt thereof.

In general formula (I), the amino acid residue $R^1$ may be of any amino acid, and includes residues wherein the carboxy group is esterified (alkyl esters are preferred); the amino alcohol residues are those wherein the carboxy group of an amino acid residue is converted to a hydroxymethyl group. Preferred amino acid residues are of neutral or acidic amino acids. α-Amino acid residues are also preferred.

Preferred amino acid residues are of glycine, alanine, valine, isoleucine, leucine, serine, threonine, proline, asparagine, glutamine, methionine, phenylalanine, tyrosine, aspartic acid, glutamic acid and esters thereof (preferably alkyl esters of from 1 to 8 carbon atoms in the esterifying alkyl group); the corresponding amino alcohols in which the carboxy groups are replaced by hydroxymethyl groups are also preferred.

In general formula (I), examples of the alkylene group of from 1 to 4 carbon atoms represented by $R^2$ are methylene, ethylene, trimethylene and tetramethylene groups and isomers thereof.

$R^2$ preferably represents a single bond, or a methylene, ethylene or propylene group.

In the general formula (I), examples of the alkyl group of from 1 to 8 carbon atoms represented by $R^3$ are methyl, ethyl, propyl, butyl, pentyl, hexyl, heptyl and octyl groups and isomers thereof, and preferred groups are pentyl, 1-methylpentyl, 2-methylpentyl, 3-methylpentyl, 4-methylpentyl, 1,1-dimethylpentyl, 1,2-dimethylpentyl, 1,3-dimethylpentyl, hexyl, 1-methylhexyl, 2-methylhexyl, 1,1-dimethylhexyl and heptyl groups.

In general formula (I), examples of the cycloalkyl group of from 4 to 7 carbon atoms (which may be substituted by alkyl of from 1 to 8 carbon atoms) are cyclobutyl, cyclopentyl, cyclohexyl and cyclohepty groups and such groups substituted by alkyl of from 1 to 8 carbon atoms, and preferred groups are cyclobutyl, 1-ethylcyclobutyl, 1-propylcyclobutyl, 1-butylcyclobutyl, 3-ethylcyclobutyl, 3-propylcyclobutyl, cyclopentyl, 3-methylcyclopentyl, 3-ethylcyclopentyl, 3-propylcyclopentyl, 3-butylcyclopentyl, 3-pentylcyclopentyl, cyclohexyl, 3-ethylcyclohexyl, 4-ethylcyclohexyl, 4-propylcyclohexyl and cycloheptyl groups.

In general formula (I), examples of the phenyl or phenoxy group (which may be substituted by at least one chlorine atom, trifluoromethyl groups or alkyl groups of from 1 to 3 carbon atoms are phenyl, 3-chlorophenoxy, 4-chlorophenoxy, 3-trifluoromethylphenoxy, 3-methylphenoxy and 4-methylphenoxy groups.

Especially preferred compounds are those in which: $R^1$ represents a glycine, leucine, proline, methionine, phenylalanine, or leucinol residue; the hydroxy group attached to the 15-position carbon atom is in α-configuration; or the grouping —$R^2$—$R^3$ represents pentyl, 2-methylhexyl or 3-butylcyclopentyl.

In this specification and the accompanying claims, the compounds of the present invention are named as amide derivatives of prostanoic acids and amino acids. The structure of prostanoic acid is shown in the formula (A) hereinbefore.

The present invention relates to all compounds of general formula I in the "natural" form or its enantiomeric form, or mixtures thereof, more particularly the racemic form consisting of equimolecular mixtures of the natural and its enantiomeric form.

As will be apparent to those skilled in the art, the compounds depicted in general formula I have at least four centres of chirality these four centres of chirality being at the alicylic ring carbon atoms identified as 8, 11 and 12 and at the C-15 carbon atom which has attached to it a hydroxy group. Further centres of chirality may occur in groups represented by $R^1$, $R^2$ and $R^3$. The presence of chirality leads, as is well known, to the existence of isomerism. However, the compounds of general formula I all have such a configuration that the side-chains attached to the ring carbon atoms in the positions identified as 8 and 12 are trans with respect to each other. All isomers of general formula I and mixtures thereof, which have those side chains attached to the ring carbon atoms in positions 8 and 12 in the trans configuration and have a hydroxy group as depicted in the 15-position are within the scope of general formula I. Preferably the hydroxy group attached to the C-15 carbon atom of formula I is in alpha configuration.

In this specification and the accompanying claims it is to be understood that:

(i) amino acids are named by their trivial names, and all of their isomers are included unless otherwise indicated;

(ii) alkyl groups may be straight or branched chain.

According to the present invention, the compounds of general formula (I) may be prepared by:

(1) when $R^1$ is as hereinbefore defined the reaction of a compound of general formula:

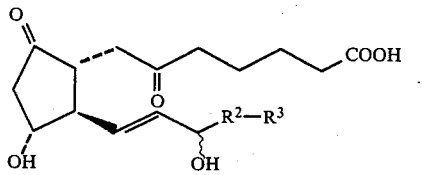
(II)

wherein the various symbols are as hereinbefore defined with an amino acid or amino alcohol of general formula:

$$R^1-H \quad (III)$$

wherein $R^1$ is as hereinbefore defined or an acid addition salt thereof to form an amide bond;

(2) (a) when $R^1$ is as hereinbefore defined the hydrolysis or alcoholysis of a compound of general formula:

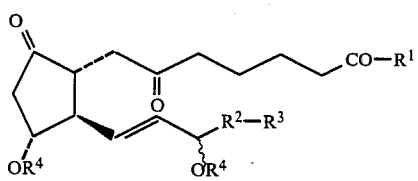
(IV)

wherein $R^4$ represents a tetrahydropyran-2-yl, tetrahydrofuran-2-yl or 1-ethoxyethyl group, and the other symbols are as hereinbefore defined; or preferably (b) when $R^1$ represents an amino acid residue in which the carboxy group is not esterified the hydrolysis of a compound of general formula:

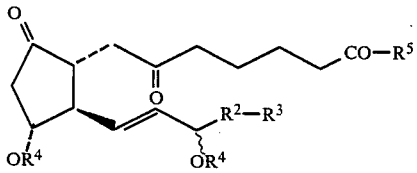
(V)

wherein $R^5$ represents an amino acid residue in which the carboxy group is not esterified and the other symbols are as hereinbefore defined; or (3) when $R^1$ represents an amino acid residue in which the carboxy group is not esterified the hydrolysis of a compound of the general formula:

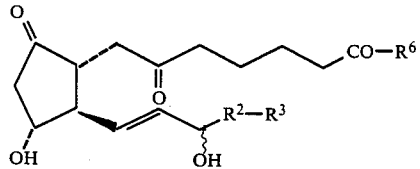
(VI)

wherein $R^6$ represents an amino acid residue in which the carboxy group is protected by a trihaloethyl group, preferably trichloroethyl, and the other symbols are as hereinbefore defined in the presence of zinc.

Reaction (1) may be carried out, for example, (A) by using a mixed acid anhydride, or (B) by using DCC (dicyclohexylcarbodiimide) as a coupling agent.

When a mixed acid anhydride is used an acid of the general formula (II) is generally reacted with an acid halide (eg. pivaloyl chloride, tosyl chloride, mesyl chloride or oxalyl chloride) or an acid derivative (eg isopropyl chloroformate, ethyl chloroformate or isobutyl chloroformate) in an inert organic solvent (eg. chloroform, methylene chloride, diethyl ether or THF) or without a solvent, in the presence of a tertiary amine (eg. pyridine, triethylamine or picoline), at a temperature of from 0° C. to 40° C. to give a mixed acid anhydride. The acid anhydride obtained is then generally reacted with an amino acid or amino alcohol of the general formula (III) in an inert organic solvent (for example as described above) at a temperature of from 0° C. to 40° C.

When DCC is used as a coupling agent, for example, an acid of the general formula (II) is reacted with an amino acid or amino alcohol of the general formula (III) in an inert organic solvent (for example as described above) or without a solvent, in the presnce of a tertiary amine (for example as described above), and DCC at a temperature of from 0° C. to 40° C.

Reactions (A) and (B) are preferably carried out in an atmosphere of an inert gas (eg. argon or nitrogen) and in anhydrous conditions.

Reaction (2) (a), i.e. hydrolysis, is a known reaction, and may be carried out, for example, using an aqueous solution of an organic acid (eg. acetic acid, p-toluenesulfonic acid, or oxalic acid) or an aqueous solution of an inorganic acid (eg. hydrochloric acid or hydrobromic acid) or a mixture thereof, in a water-miscible inert organic solvent (eg. THF, dioxan or acetone), at a temperature of from 0° C. to 90° C. A compound of the general formula (I), wherein $R^1$ is an amino acid residue wherein the carboxy group is converted to an ester or hydroxymethyl group may also be prepared by alcoholysis.

Alcoholysis is a known reaction, and may be carried out, for example, using an organic acid (eg. p-toluenesulfonic acid, or trifluoroacetic acid) in an absolute alkanol (eg. methanol or ethanol), at a temperature of from 0° C. to 90° C.

Reaction (2) (b), i.e. hydrolysis, may be carried out by the same procedure described for reaction (2) (a).

Reaction (3), i.e. hydrolysis, is a known reaction, and may be carried out, for example, using an aqueous solution of a weak acid (eg. acetic acid or hydrobromic acid), in the presence of zinc, in an inert organic solvent (eg. THF, dioxan or acetone) or without a solvent, at a temperature of from 0° C. to 70° C.

The intermediate compounds of the general formula (II), (IV), (V) and (VI) may be prepared by the series of reaction steps shown in the following scheme [A].

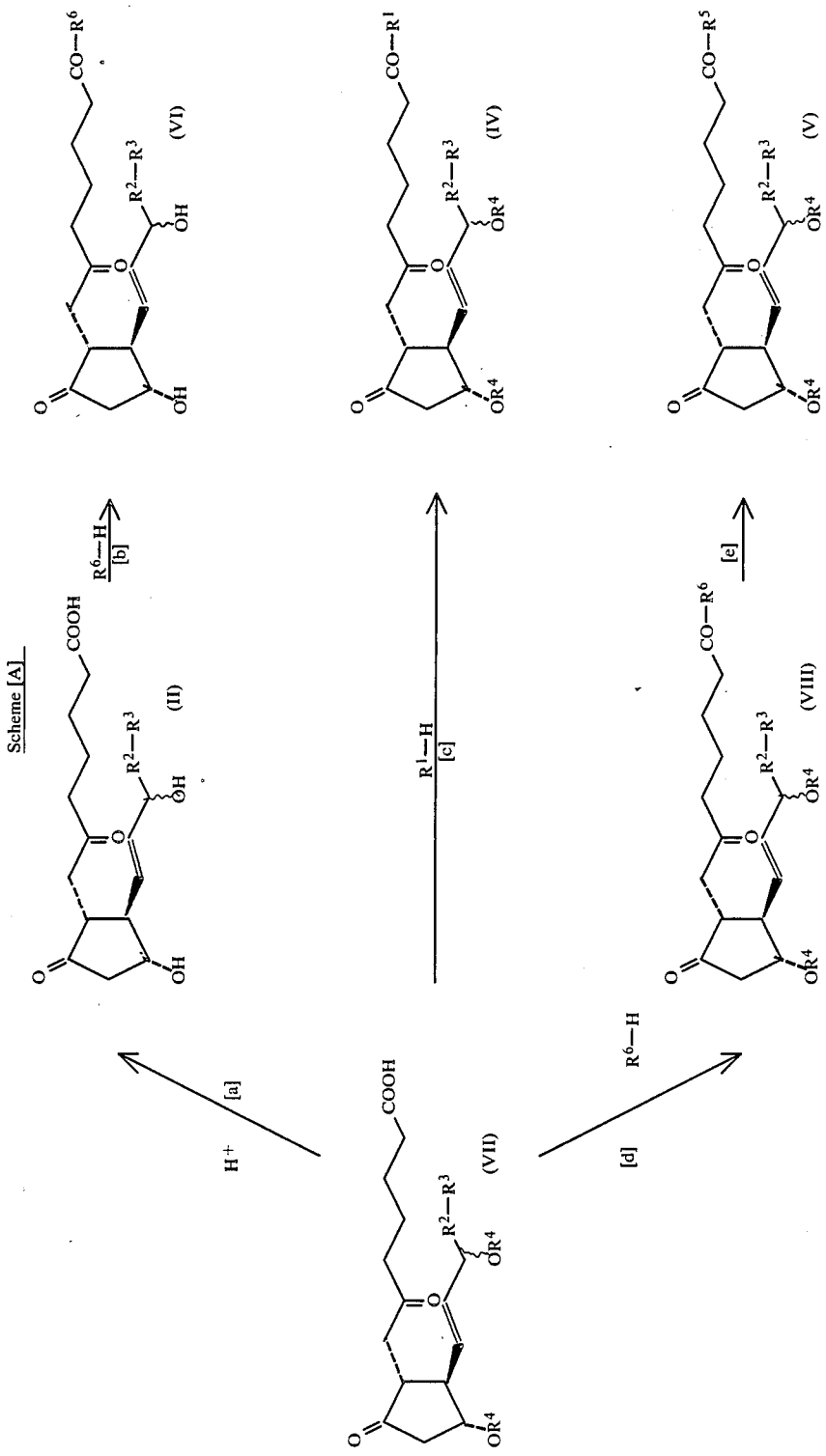

In scheme (A), each reaction step is known per se, and may be carried out as follows:

Step [a] may be carried out under the conditions hereinbefore described for the hydrolysis of compounds of the general formula (IV), to obtain the compounds of general formula (I).

Steps [b], [c] and [d] may be carried out under the conditions hereinbefore described for the conversion of the compounds of the general formula (II) and the compounds of the general formula (III) to the compounds of general formula (I).

Step [e] may be carried out under the conditions hereinbefore described for the conversion of compounds of the general formula (VI) to the compounds of the general formula (I).

Compounds of the general formula (IV) wherein $R^1$ is an amino acid residue in which the carboxy group is not esterified (represented by $R^5$) and wherein $R^1$ is an amino acid residue in which the carboxy group is optionally esterified (represented by $R^7$) may be prepared by the series of reaction steps described in the following scheme [B].

In scheme [B], $X^1$ represents a halogen atom.

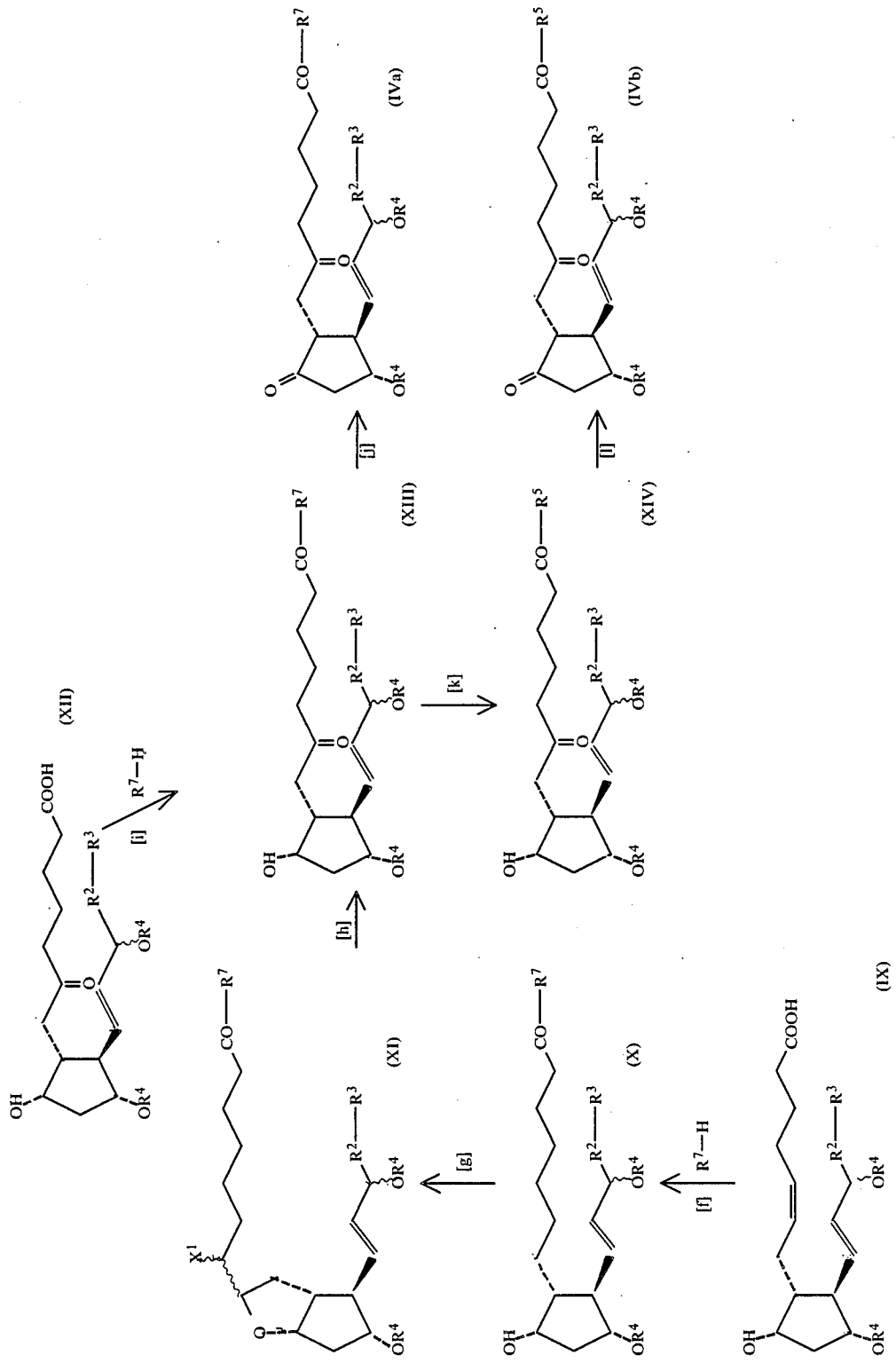

In scheme [B], each reaction step is known per se, and may be carried out as follows.

Steps [f] and [i] may be carried out under the conditions hereinbefore described for the preparation of compounds of the general formula (I) from the compounds of the general formula (II).

Step [g], a simultaneous halogenation and cyclization, may be carried out, for example, using a halogenating agent (eg. iodine, bromine or N-bromosuccinimide) in an inert organic solvent (eg. methylene chloride, THF or carbon tetrachloride) at a temperature of from 0° C. to 40° C.

Step [h], a dehydrohalogenation and hydrolysis, may be carried out, for example, using a dehydrohalogenating agent (eg. 1,5-diazabicyclo[5.4.0]undecene-5, 1,5-diazabicyclo[4.3.0]nonene-5 or 1,4-diazabicyclo[2.2.2]octane, in an inert organic solvent (eg. toluene or benzene) or without solvent, at a temperature of from room temperature to 100° C., and the hydrolysis may be carried out by the procedures hereinbefore described.

Steps [j] and [l], oxidation, may be carried out, for example, by Jones's oxidation, Swern's oxidation or Collins's oxidation.

Step [k], hydrolysis of a carboxylic ester in $R^7$ to a free carboxylic acid may be carried out, for example, using an aqueous solution of an alkali (eg. sodium hydroxide, potassium hydroxide, potassium carbonate or sodium carbonate) in a water-miscible organic solvent (eg. THF, dioxan or methanol). This step is of course not required when $R^7$ already comprises a free carboxy group.

In the reactions described in this specification products may be purified by conventional methods, for example, distillation at atmospheric or reduced pressure. high performance liquid chromatography, thin layer or column chromatography using silica gel or magnesium silicate or by washing or recrystallization. Purification may be carried out after each reaction or after a series of reactions.

The starting materials and reagents used in the preparative procedures hereinbefore described are known compounds or may be prepared by methods known per se.

For example, the compounds of general formula (VII) are described as compounds of general formula (III) in Japanese Patent Kokai No. 54-44639 and British Pat. No. 2,006,753. The compound wherein —$R^2$—$R^3$ is a 3-butylcyclopentyl group and $R^4$ is a tetrahydropyran-2-yl group is described in reference example 26 of Japanese Patent Kokai No. 59-163365 and European Patent Publication No. 0,122,019.

The compound of the general formula (IX) are described as compounds of general formula (XI) in Japanese Patent Kokai No. 53-95958 and U.S. Pat. No. 4,399,147.

The compounds of the general formula (XII) are described as compounds of general formula (IV) in Japanese Patent Kokai No. 54-44639 and British Pat. No. 2,006,753.

Cyclodextrin clathrates of the novel 6-keto-prostaglandin $E_1$ derivatives of general formula (I) may be prepared by the method described in Japanese Patent Kokoku No. 50-3362 or Japanese Patent Kokai No. 47-39057, or British Pat. No. 1,351,238 or 1,419,221, using α-, β- or γ-cyclodextrins or a mixture thereof. Conversion into their cyclodextrin clathrates serves to increase the stability and solubility in water of the 6-keto-prostaglandin $E_1$ derivatives of the general formula (I), and is therefore useful to facilitate administration as a pharmaceutical.

The compounds of general formula (I) wherein $R^1$ represents an amino acid residue containing a free carboxy group may be converted into salts.

Conversion into salts increases the solubility of the compounds of the present invention in water and therefore facilitates administration as a pharmaceutical.

The compounds of the present invention may readily be converted into corresponding salts by methods known per se, e.g. by methods described hereinafter.

The salts are preferably non-toxic salts, i.e. salts of cations which are relatively innocuous to living body tissues (in animals including human beings) and are such that the effective pharmacological properties of the compounds of the general formula (I) are not impaired by side effects resulting from the cations when used at the doses required in therapy or prophylaxis. Water-soluble salts are preferred.

Suitable salts include, for example, a salt of an alkali metal such as sodium or potassium, a salt of an alkaline earth metal such as calcium or magnesium, an ammonium salt and a pharmaceutically acceptable (non-toxic) amine salt.

Amines suitable for forming such salts with a carboxy group are well known and include, for example, those amines which are theoretically obtained by substituting one or more of the hydrogen atoms of ammonia by other groups. These groups, which may be the same or different when one or more hydrogen atoms are substituted, are selected from, for example, alkyl groups of from 1 to 6 carbon atoms and hydroxyalkyl groups of from 1 to 3 carbon atoms. Suitable non-toxic amine salts include salts of tetraalkylammonium group, such as the tetramethylammonium salt and salts of an organic amine, such as methylamine, dimethylamine, cyclopentylamine, benzylamine, phenethylamine, piperidine, monoethanolamine, diethanolamine, lysine and arginine.

Salts can be obtained from the compounds of the general formula (I), by methods known per se, for example, by reacting the compound of general formula (I) and a suitable base such as a hydroxide or carbonate of an alkali metal or alkaline earth metal, ammonium hydroxide, ammonia or an organic amine in theoretical amounts in an appropriate solvent.

The salts can be isolated by freeze-drying the solution, or by filtration if the salts are sufficiently insoluble in the reaction solution, or if necessary, by removing part of the solvent followed by filtration.

The compounds of general formula (I) wherein $R^1$ represents an amino acid residue containing a free carboxy group may also be converted by known methods into esters thereof.

The compounds of general formula (I), cyclodextrin clathrates thereof and non-toxic salts thereof possess a strong cytoprotective activity associated with very weak other activities typical of the prostaglandins, and are therefore useful for the treatment of cytodamage (i.e. for the treatment of diseases associated with cytodamage).

The 6-keto-prostaglandin $E_1$ derivatives of the general formula (I), cyclodextrin clathrates thereof and non-toxic salts thereof are useful or the prevention and/or treatment of many diseases which are associated with cytodamage as follows:

(1) digestive system diseases (for example, liver diseases such as hepatitis, fatty liver, liver cirrhosis, liver abscess and pancreatic diseases such as pancreatitis)

(2) urologic diseases (for example, nephritis, diabetic nephropathies, cystitis and urethritis)

(3) respiratory tract diseases (for example, pneumonia, empyema and rhinitis)

(4) cardiovascular diseases (for example, arrhythmia, cerebral aneurysm and cerebral embolism)

(5) haemotologic diseases (for example anemia)

(6) other diseases (for example, diabetes mellitus and complications caused by diabetes mellitus).

As the compounds of the present invention possess substantially reduced side effects in comparison with known compounds they are expected to be effective in the treatment of cytodamage.

The results shown in the Table I were obtained using the following standard laboratory tests:

(i) cytoprotective activity in carbon tetrachloride-induced acute liver damage in rats.

(ii) hypotensive activity in dogs and (iii) inhibitory activity of blood platelet aggregation induced by ADP in rats. The experimental methods are described hereinafter.

GPT (glutamic pyruvic transaminase) activity were measured. The minimum effective dose was the minimum dose which had a significant effect on the plasma GOT and GPT levels.

(ii) Hypotensive activity was measured in the anesthetized dog by intravenous administration, and as active control, $PGE_1$ was used. The hypotensive activity relative to $PGE_1$ is shown in Table I.

(iii) The concentrations required to inhibit blood platelet aggregation induced in rats by ADP (adenosine diphosphate) are shown relative to $PGE_1$.

As is clear from Table I, the compounds (a), (b) and (c) possess almost the same activity in the inhibition of liver damage induced by carbon tetrachloride when compared with compounds (d) and (e). In sharp contrast, however compounds (a), (b) and (c) possess only ca. 1/700-1/2450 of the activity of compounds (d) and (e) in lowering blood pressure and only ca. 1/292-1/6300 of the activity of compounds (d) and (e) in inhibiting blood platelet aggregation.

The compounds of the invention therefore possess a similar level of useful cytoprotective activity to the known comparison compounds but are much less active (more than one hundred fold less active) in causing the

TABLE I

| Compound | (i) Inhibiting activity of $CCl_4$ induced liver damage (s.c., minimum effective dose, μg/Kg) | (ii) Hypotensive activity ($PGE_1 = 1$) | (iii) Inhibiting activity of blood platelet aggregation ($PGE_1 = 1$) |
| --- | --- | --- | --- |
| (a) Compound prepared in example 1 | <10 | 0.03 | 0.01 |
| (b) Compound prepared in example 1(b) | <10 | 0.01 | 0.01 |
| (c) Compound prepared in example 2(a) | 30 | 0.014 | 0.0053 |
| (d) [structure] (This compound was prepared by the method described in Japanese Patent Kokai No. 54-44639, i.e. British Patent No. 2,006,753.) | 30 | 21 | 68 |
| (e) [structure] (Compound described in example 1 in Japanese Patent Kokai No. 59-163365, i.e. European Patent Publication No. 0,122,019.) | 5 | 24.5 | 506 |

(i) Inhibitory activity on liver damage induced by carbon tetrachloride.

A solution of carbon tetrachloride (2000 μl) dissolved in olive oil (10 ml) was administered to Wistar male rates (body weight 190-220 g) at a rate of 2000 μl/kg animal body weight by intraperitoneal injection.

A solution of a compound of the present invention or of one of the comparison compounds in olive oil (2 ml/kg animal body weight) was administered three times, at the same time as, and then 6 hrs and 12 hrs after, the dosage of carbon tetrachloride, and blood was collected twice after 24 hrs and 48 hrs after the first dosage. The blood was centrifuged and plasma GOT (glutamic oxalacetic transaminase) activity and plasma side effects of lowered blood pressure or inhibiting blood platelate aggregation.

The toxicity of the compounds of the present invention is very low and compounds of the present invention may be considered to be sufficiently safe and suitable for pharmaceutical use.

For example, the values of $LD_{50}$ of the compounds prepared in examples 1 and 1(b) were 22 mg/kg and 30 mg/kg animal body weight respectively by intravenous administration in mice.

The following Reference Examples and Examples illustrate the preparation of compounds of the present invention. In the reference examples and examples, 'mp', 'TLC', 'IR', 'NMR' and 'MS' represent 'melting point', 'thin layer chromatography', 'infrared absorption spectrum', 'nuclear magnetic resonance' and 'mass spectrum', respectively. Where solvent ratios are specified in chromatographic separations, the ratios are by volume and the solvents in parentheses show the eluting or developing solvents used. Except when specified otherwise, infrared spectra are recorded by the liquid film method and nuclear magnetic resonance spectra are recorded in deuterochloroform (CDCl₃) solution.

te=9:1) to give the title compound (3.51 g) having the following physical data:

TLC: Rf 0.90 (CH₃Cl:CH₃OH=10:1);

NMR: δ 7.6–7.0 (10H, m), 5.05 (2H, s), 4.9–4.6 (2H, m), 4.3–4.0 (2H, m), 3.4–3.0 (2H, m);

MS: m/z 431, 429, 340, 338, 280, 278, 210, 181, 151, 91.

Reference Example 1(a)–1(e)

Following the procedure of reference example 1, using the appropriate amino acid, the compounds shown in the following Table II were prepared.

TABLE II

| No. | Name & Structural formula | TLC | NMR | MS |
|---|---|---|---|---|
| 1(a) | N—benzyloxycarbonylglycine 2,2,2-trichloroethyl ester<br>Cbz—NH—CH₂—COO—CH₂CCl₃ | Rf 0.79<br>(CHCl₃:CH₃OH = 10:1) | δ 7.3(5H,s), 5.1(2H,s) 4.8(2H,s), 4.25–3.9(2H, m) | m/z 341, 339,192, 164,108, 91 |
| 1(b) | N—benzyloxycarbonyl-L—leucine 2,2,2-trichloroethyl ester<br>Cbz—NH—CH—COO—CH₂CCl₃<br>        │<br>      CH₂CH(CH₃)₂ | Rf 0.87<br>(CHCl₃:CH₃OH = 10:1) | δ 7.3(5H,s), 5.1(2H,s) 4.8(2H,s), 4.7–4.3(1H, m), 1.0(6H,d) | m/z 397, 395,220, 176,108, 91 |
| 1(c) | N—benzyloxycarbonyl-L—proline 2,2,2-trichloroethyl ester<br>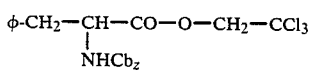 | Rf 0.55<br>(n-C₆H₁₄:EtOAc = 2:1) | δ 7.5–7.1(5H,m), 5.2–5.0 (2H,m), 4.8(1H,q), 4.65–4.4(3H,m), 3.9–3.3(3H, m) | m/z 381, 379,246, 244,204, 160 |
| 1(d) | N—benzyloxycarbonyl-L—methionine 2,2,2-trichloroethyl ester<br>Cbz—NH—CH—COO—CH₂CCl₃<br>        │<br>      CH₂CH₂SCH₃ | Rf 0.69<br>(n-C₆H₁₄:EtOAc = 2:1) | δ 7.38(5H,s), 5.15(2H, s), 4.8(2H,q) | m/z 415, 413,280, 278,263, 261,131, 91 |
| 1(e) | N—benzyloxycarbonyl-D—leucine 2,2,2-trichloroethyl ester<br>Cbz—NH—CH—COO—CH₂CCl₃<br>        │<br>      CH₂—CH(CH₃)₂ | Rf 0.80<br>(EtOAc:n-C₆H₁₄ = 1:1) | δ 7.35(5H,s), 5.4–4.25 (6H,m), 0.95(6H,d) | m/z 397, 395,248, 220,186, 176,108, 91 |

Reference Example 1

Synthesis of N-benzyloxycarbonyl-L-phenylalanine 2,2,2-trichloroethyl ester

φ-CH₂—CH—CO—O—CH₂—CCl₃
       │
     NHCbz

In an atmosphere of argon, a solution of N-benzyloxycarbonyl-L-phenylalanine (5.69 g) in acetone (100 ml) was cooled to 0° C. To the solution, triethylamine (6.35 ml) and isopropyl chloroformate (4.98 ml) were added, and the mixture was stirred for 20 mins. To the reaction mixture, triethylamine (12.6 ml) and 2,2,2-trichloroethanol (7.28 ml) were added, and the mixture was stirred for 1 hr at the same temperature, and another 1 hr at room temperature. The reaction solution was diluted with ethyl acetate, the diluted solution was washed with water and saturated brine, successively, dried and evaporated. The residue was purified by column chromatography on silica gel (hexane:ethyl aceta- Reference Example 2

Synthesis of L-phenylalanine 2,2,2-trichloroethyl ester hydrobromide

φ-CH₂—CH—CO—O—CH₂—CCl₃
       │
     NH₂.HBr

In an atmosphere of argon, a mixture of the compound prepared in reference example 1 (3.51 g) and hydrobromic acid-acetic acid (6.2 ml; HBr 30% w/w) was stirred for 30 mins at room temperature. To the solution, a mixture of hexane-ethyl ether (1:1) was added and then the mixture was allowed to stand. Crystals deposited were gathered by filtration, and washed with a mixture of hexane-ethyl ether (1:1) and dried to give the title compound (1.45 g) having the following physical data:

NMR: δ 7.30 (5H, s), 4.80 (2H, s), 4.47 (1H, t), 3.40 (2H, d);

MS: m/z 297, 295, 262, 260, 208, 206, 204, 120, 103, 91.

Reference Example 2(a)–2(e)

Following the procedure of reference example 2, using the appropriate compound prepared in reference examples 1(a)–1(e), the compounds shown in the following table III were prepared.

TABLE III

| No. | Name & Structural formula | TLC | NMR | MS |
|---|---|---|---|---|
| 2(a) | glycine 2,2,2-trichloroethyl ester hydrobromide<br>$H_2N-CH_2-COO-CH_2CCl_3$<br>HBr | | δ 4.85(2H,s), 4.0(2H,s) | m/z 207,205, 172,170,141, 91 |
| 2(b) | L—leucine 2,2,2-trichloroethyl ester hydrobromide<br>$H_2N-CH-COO-CH_2CCl_3$<br>HBr   $CH_2CH(CH_3)_2$ | | δ 5.03(1H,d), 4.73(1H, d), 4.36(1H,t), 2.4–1.8 (3H,m), 1.2–0.8(6H,m) | m/z 264,262, 228,226,206, 204,133,131, 86 |
| 2(c) | L—proline 2,2,2-trichloroethyl ester hydrobromide<br>HBr.HN—(pyrrolidine)—COOCH$_2$CCl$_3$ | Rf 0.03 (n-C$_6$H$_{14}$:EtOAc = 2:1) | δ 9.4–8.5(1H,s), 10.6– 9.8(1H,s), 5.25–4.4(3H, m), 4.0–3.25(2H,m) | m/z 245,247 210 |
| 2(d) | L—methionine 2,2,2-trichloroethyl ester hydrobromide<br>$NH_2-CH-COO-CH_2CCl_3$<br>HBr   $CH_2CH_2SCH_3$ | Rf 0.21 (EtOAc) | | m/z 307,305,283, 281,279 |
| 2(e) | D—leucine 2,2,2-trichloroethyl ester hydrobromide<br>$H_2N-CH-COO-CH_2CCl_3$<br>   $CH_2CH(CH_3)_2$ | | δ 5.05(1H,d), 4.7(1H, d), 4.6–4.2(1H,m), 1.05(6H,d) | m/z 248,246, 228,226,206, 204,86 |

Reference Example 3

Synthesis of N-[(13E)-(11α,15α,16S,18S)-6,9-dioxo-11,15-bis(tetrahydropyran-2-yloxy)-16,18-ethano-20-ethylprost-13-en-1-oyl]-L-phenylalanine 2,2,2-trichloroethyl ester

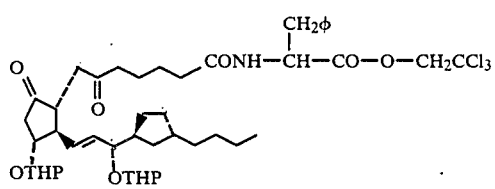

In an atmosphere of argon, a solution of (13E)-(11α,15α,16S,18S)-6,9-dioxo-11,15-bis(tetrahydropyran-2-yloxy)-16,18-ethano-20-ethylprost-13-enoic acid (100 mg; compound described in reference example 26 in Japanese Patent Kokai No. 59-163365 and European Patent Publication No. 0,122,019) in acetone (5 ml) was stirred at 0° C. Triethylamine (56.7 μl) were added dropwise to the solution, and the mixture was stirred for 20 mins at the same temperature. After stirring, triethylamine (296 μl), and the compound prepared in reference example 2 (215 mg) secondly were added to the reaction mixture. The mixture was stirred for 20 mins at room temperature. After addition of dimethylformamide (1 ml), the mixture was stirred for 1 hr and 40 mins at the same temperature. The reaction mixture was diluted with ethyl acetate, and the diluted solution was washed with water, a dil. hydrochloric acid, water and a saturated brine, successively, dried and then evaporated. The residue was purified by column chromatography on silica gel (hexane:ethyl acetate=1:1) to give the title compound (110 mg) having the following physical data:

TLC: Rf 0.50 (n-C$_6$H$_{14}$:EtOAc=1:1);

NMR: δ 7.4–7.05 (5H, m), 6.04 and 6.0 (1H), 5.9–5.2 (2H, m), 5.1–4.95 (1H, m), 4.9–4.5 (4H, m), 3.6–3.35 (2H, m), 3.35–3.0 (2H, m), 0.9 (2H, t);

MS: m/z 685, 683, 681, 667, 574, 576, 558, 556, 120, 91, 85.

Reference Example 3(a)–3(e)

Following the procedure of reference example 3, using the appropriate compound prepared in reference examples 2(a)–2(e), the compounds shown in the following Table IV were prepared.

TABLE IV

| No. | Name & Structural formula | TLC | NMR | MS |
|---|---|---|---|---|
| 3(a) | N—[(13E)-(11α,15α,16S,18S)—6,9-dioxo-11,15-bis(tetrahydropyran-2-yloxy)-16, | Rf 0.21 (n-C$_6$H$_{14}$: | δ 6.35–6.15(1H,m), 5.7–5.2(2H,m), 4.8(2H, | m/z 593,591, 575,573,426 |

| No. | Name & Structural formula | TLC | NMR | MS |
|---|---|---|---|---|
| | 18-ethano-20-ethylprost-13-en-1-oyl]glycine 2,2,2-trichloroethyl ester | EtOAc = 1:1 | s), 4.8–4.5(2H,m), 4.3–3.65(6H,m), 3.65–3.35 (2H,m), 0.9(3H,t) | 318,316,111, 85 |
| 3(b) | N—[(13E)-(11α,15α,16S,18S)—6,9-dioxo-11,15-bis(tetrahydropyran-2-yloxy)-16,18-ethano-20-ethylprost-13-en-1-oyl]L-leucine 2,2,2-trichloroethyl ester | Rf 0.53 (n-C$_6$H$_{14}$: EtOAc = 1:1) | δ 6.25–5.9(1H,m), 5.9–5.1(2H,m), 5.0–4.5(4H, m), 1.05–0.7 (9H,m) | m/z 649,647, 631,629,524, 522,454,196 111,86 |
| 3(c) | N—[(13E)-(11α,15α,16S,18S)—6,9-dioxo-11,15-bis(tetrahydropyran-2-yloxy)-16,18-ethano-20-ethylprost-13-en-1-oyl]-L-proline 2,2,2-trichloroethyl ester | Rf 0.37 (EtOAc: n-C$_6$H$_{14}$ = 2:1) | δ 5.8–5.1(2H,m), 5.1–4.4(5H,m), 0.9(3H,t) | m/z 631,615, 613,581,579, 508,506,358, 356 |
| 3(d) | N—[(13E)-(11α,15α,16S,18S)—6,9-dioxo-11,15-bis(tetrahydropyran-2-yloxy)-16,18-ethano-20-ethylprost-13-en-1-oyl]-L-methionine 2,2,2-trichloroethyl ester | Rf 0.53 (EtOAc: n-C$_6$H$_{14}$ = 2:1) | δ 6.6–6.2(1H,m), 5.8–5.2(2H,m), 5.1–4.5(5H,m), 0.9(3H,t) | m/z 667,665, 649,647,631, 615,613,370 |
| 3(e) | N—[(13E)-(11α,15α,16S,18S)—6,9-dioxo-11,15-bis(tetrahydropyran-2-yloxy)-16,18-ethano-20-ethylprost-13-en-1-oyl]-D-leucine 2,2,2-trichloroethyl ester | Rf 0.34 (n-C$_6$H$_{14}$ EtOAc = 1:1) | δ 6.04(1H,d), 5.7–5.2 (2H,m), 4.95–4.5(5H, m), 4.3–3.7(4H,m), 3.6–3.3(2H,m), 1.05–0.8 (9H,m) | m/z 650,648, 631,629,524, 522,374,372 |

Reference Example 4

Synthesis of N-[(13E)-(11α,15α,16S,18S)-6,9-dioxo-11,15-bis(tetrahydropyran-2-yloxy)-16,18-ethano-20-ethylprost-13-en-1-oyl]-L-leucinol

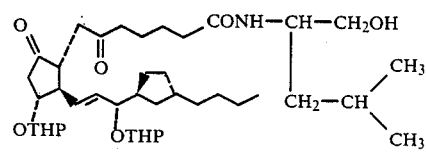

In an atmosphere of argon, triethylamine (179 μl), and isopropyl chloroformate (139 μl) secondly were added to a solution of (13E)-(11α,15α,16S,18S)-6,9-dioxo-11,15-bis(tetrahydropyran-2-yloxy)-16,18-ethano-20-ethylprost-13-enoic acid (315 mg; described hereinbefore) in acetone (15 ml), and the mixture was stirred for 20 mins at 0° C. Triethylamine (315 μl) and L-leucinol (272 μl) secondly, were added to the reaction solution; the mixture was stirred for 1 hr at room temperature. After reaction, water was added to the reaction mixture, and the mixture was added to the reaction mixture, and the mixture was diluted with ethyl acetate. The diluted solution was washed with water and a saturated brine successively, dried and then evaporated. The residue was purified by column chromatography on silica gel (EtOAc:n-C$_6$H$_{14}$=3:1) to give the title compound (200 mg) having the following physical data:

TLC: Rf 0.39 (EtOAc);
NMR: δ 5.8 (1H, d), 5.7–5.2 (2H, m), 4.8–4.5 (2H, m), 4.3–3.3 (9H, m), 1.0–0.8 (9H, m);
MS: m/z 671, 587, 569, 503, 485, 454, 378.

Reference Example 5

Synthesis of N-[(13E)-(9a,11a,15a,17S)-6-oxo-9-hydroxy-11,15-bis(tetrahydropyran-2-yloxy)-17,20-dimethylprost-13-en-1-oyl]-L-phenylalanine methyl ester

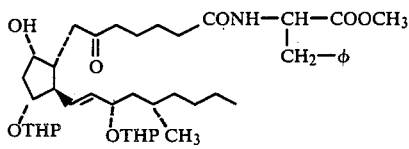

A solution of (13E)-(9α,11α,15α,17S)-6-oxo-9-hydroxy-11,15-bis(tetrahydropyran-2-yloxy)-17,20-dimethylprost-13-enoic acid (1 g; prepared by the method described in Japanese patent Kokai No. 54-44639 and British Pat. No. 2,006,753) in methylene chloride (10 ml) was cooled with ice. To the solution, triethylamine (429 mg) and pivaloyl chloride (245 mg) secondly, were added, and the mixture was stirred for 30 mins at room temperature. L-phenylalanine methyl ester (476 mg) was added to the reaction solution, the mixture was stirred for 30 mins at room temperature and then diluted with ethyl ether. The diluted solution was washed with water, an aq. solution of sodium bicarbonate, 1N hydrochloric acid, an aq. solution of sodium bicarbonate and water, successively, dried and then evaporated. The residue was purified by column chromatography on silica gel (cyclohexane:EtOAc=1:2) to give the title compound (647 mg) having the following physical data:

NMR: δ 7.38–7.02 (5H, m), 6.15–5.90 (1H, m), 5.65–5.25 (2H, m), 5.00–4.80 (1H, m), 4.75–4.55 (2H, m), 3.73 (3H, s), 3.20–3.05 (2H, m), 1.00–0.80 (6H, m);
IR (liquid film method): 3600–2300, 1740, 1720, 1650, 1600, 1530, 1450, 1435, 1200, 1130, 1080, 1030, 1020, 980, 870, 810 cm$^{-1}$;
MS: m/z 709, 678, 607, 541, 523, 505, 343, 327, 246, 180.

Reference Example 6

Synthesis of N-[(13E)-(11α,15α,17S)-6,9-dioxo-11,15-bis(tetrahydropyran-2-yloxy)-17,20-dimethylprost-13-en-1-oyl]-L-phenylalanine methyl ester

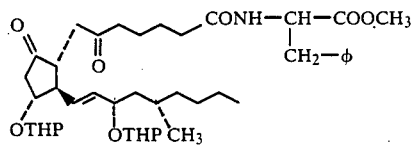

A solution of the compound prepared in reference example 5 (501 mg) in acetone (10 ml) was cooled to −25° C., and Jone's reagent (1 ml; 2.67N) was added to the solution dropwise, and the mixture was stirred for 1.5 hrs at the same temperature. Isopropyl alcohol was added to the solution in order to stop the reaction. The solution diluted with ethyl ether was washed with water, an aq. solution of sodium bicarbonate and water, successively, dried and then evaporated. The residue was purified by column chromatography on silica gel (cyclohexane:EtOAc=1:1) to give the title compound (322 mg) having the following physical data:

NMR: δ 7.35–7.20 (3H, m), 7.20–7.05 (2H, m), 6.15–5.95 (1H, d), 5.70–5.30 (2H, m), 5.00–4.80 (1H, m), 4.80–4.60 (2H, m), 4.30–4.00 (2H, m), 3.72 (3H, s), 3.20–3.05 (2H, m), 1.00–0.80 (6H, m);
IR (liquid film method): 3600–2300, 1740, 1710, 1650, 1520, 1450, 1435, 1370, 1350, 1200, 1120, 1070, 1030, 1015, 970, 910, 870, 810, 740 cm$^{-1}$;
MS: m/z 641, 623, 592, 539, 521, 180, 120, 85.

Reference Example 7

Synthesis of N-[(5Z,13E)-(9α,11α,15α,17S)-9-hydroxy-11,15-bis(tetrahydropyran-2-yloxy)-17,20-dimethylprosta-5,13-dienoyl]glycine methyl ester

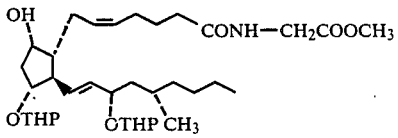

Triethylamine (550 mg) was added to a solution of (5Z,13E)-(9α,11α,15α,17S)-9-hydroxy-11,15-bis(tetrahydropyran-2-yloxy)-17,20-dimethylprosta-5,13-dienoic acid (1.2 g; prepared by the method described in Japanese Patent Publication No. 53-95958 and U.S. Pat. No. 4,399,147) in THF (10 ml). Pivaloyl chloride (316 mg) was added to the solution cooled with ice, the mixture was stirred for 30 mins at room temperature. Glycine methyl ester hydrochloride (330 mg) was added to the solution, and the mixture was stirred for 1 hr at room temperature and for 1 hr at 40° C., and then diluted with ethyl ether. The diluted solution was washed with water, an aq. solution of sodium bicarbonate and water, successively, dried and then evaporated. The residue was purified by column chromatography on silica gel (cyclohexane:EtOAc=1:2) to give the title compound (1.1 g) having the following physical data:

NMR: δ 6.4–6.2 (1H, m), 5.7–5.2 (4H, m), 4.8–4.6 (2H, m), 4.2–4.0 (4H, m), 3.77 (3H, s), 1.0–0.8 (6H, m);
IR (liquid film method): 3600–2300, 1750, 1660, 1540, 1440, 1360, 1200, 1130, 1070, 1020, 970, 910, 870, 810 cm$^{-1}$;
MS: m/z 548, 537, 536, 519, 488, 435, 417, 399, 363.

Reference Example 8

Synthesis of N-[(13E)-(9α,11α,15α,17S)-5-iodo-6,9-epoxy-11,15-bis(tetrahydropyran-2-yloxy)-17,20-dimethylprost-13-en-1-oyl]glycine methyl ester

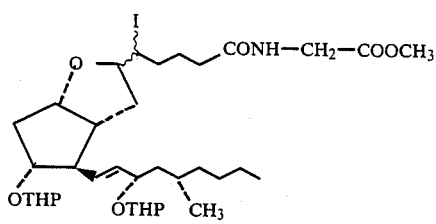

To an ice-cooled solution of the compound prepared in reference example 7 (1.1 g) in methylene chloride (10 ml), a solution of iodine (489 mg) in methylene chloride (55 ml) was added over a period of 3 hrs. Thereafter, a solution of sodium thiosulfate (2.9 g) in water (20 ml) was added to the solution. To the solution, methylene chloride was added. The oily layer which separated was dried and evaporated. The residue was purified by column chromatography on silica gel (cyclohexane:EtOAc=1:1) to give the title compound (1.0 g) having the following data:

NMR: δ 6.2–6.0 (1H, m), 5.7–5.2 (2H, m), 4.8–4.6 (2H, m), 4.3–4.0 (3H, m), 3.77 (3H, s), 1.0–0.8 (6H, m);

IR (liquid film method): 3600–2300, 1750, 1740, 1660, 1535, 1440, 1370, 1200, 1130, 1080, 1030, 1020, 980, 910, 870, 815 cm$^{-1}$;

MS: m/z 564, 505, 434, 433, 416, 415, 399.

Reference Example 9

Synthesis of N-[(13E)-(9α,11α,15α,17S)-6-oxo-9-hydroxy-11,15-bis(tetrahydropyran-2-yloxy)-17,20-dimethylprost-13-en-1-oyl]glycine methyl ester

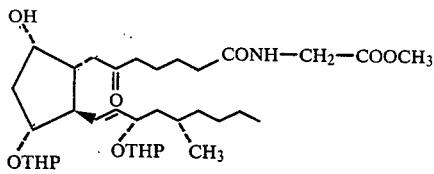

A mixture of the compound prepared in reference example 8 (985 mg), DBU (1.9 g; 1,5-diazabicyclo[5.4.0]undecene-5) and toluene (5 ml) was stirred overnight at 50° C. To the reaction solution diluted with ethyl acetate, 1N hydrochloric acid and ice-water were added. The mixture was shaken in a separating funnel. The oily layer separated was washed with water, dried and evaporated. The residue was purified by column chromatography on silica gel (EtOAc) to give the title compound (600 mg) having the following physical data:

NMR: δ 6.3–6.1 (1H, m), 5.7–5.2 (2H, m), 4.8–4.2 (2H, m), 4.3–4.0 (3H, m), 3.76 (3H, s), 1.0–0.8 (6H, m);

IR (liquid film method): 3600–2300, 1750, 1710, 1660, 1540, 1440, 1370, 1200, 1180, 1130, 1080, 1030, 1020, 980, 910, 870, 810 cm$^{-1}$;

MS: m/z 619, 534, 518, 517, 451, 450, 433, 416, 415, 399.

Reference Example 10

Synthesis of N-[(13E)-(11α,15α,17S)-6,9-dioxo-11,15-bis(tetrahydropyran-2-yloxy)-17,20-dimethylprost-13-en-1-oyl]glycine methyl ester

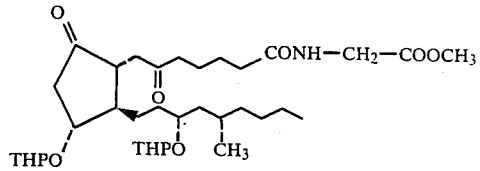

Jones's reagent (1 ml; 2.67N) was added dropwise to a −25° C.-cooled solution of the compound prepared in reference example 9 (577 mg) in acetone (10 ml), and the mixture was stirred for 1 hr and 40 mins at the same temperature. Isopropyl alcohol was added to the reaction solution in order to stop the reaction. The reaction solution diluted with ethyl ether was washed with water, an aq. solution of sodium bicarbonate and water, successively, dried and evaporated. The residue was purified by column chromatography on silica gel (EtOAc) to give the title compound (403 mg) having the following physical data:

NMR: δ 6.3–6.1 (1H, m), 5.7–5.3 (2H, m), 4.8–4.6 (2H, m), 4.3–4.1 (1H, m), 4.05 (2H, d), 3.76 (3H, s), 1.0–0.8 (6H, m);

IR (liquid film method): 3600–2300, 1740, 1710, 1670, 1530, 1450, 1440, 1370, 1200, 1130, 1070, 1030, 1020, 970, 910, 870, 810 cm$^{-1}$;

MS: m/z 551, 533, 502, 449, 431, 369, 350.

Reference Example 11

Synthesis N-[(13E)-(11α,15α)-6,9-dioxo-11,15-bis(tetrahydropyran-2-yloxy)prost-13-en-1-oyl]-L-leucine

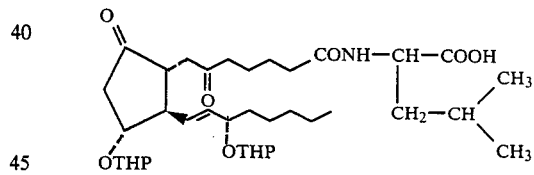

A solution of (13E)-(11α,15α)-6,9-dioxo-11,15-bis(tetrahydropyran-2-yloxy)prost-13-enoic acid (268 mg; prepared by the method described in Japanese Patent Kokai No. 54-44639 and British Pat. No. 2,006,753) in dry acetone (2.5 ml) was cooled to −10° C. To the solution, triethylamine (77 μl), and isobutyl chloroformate (71 μl) secondly were added, and the mixture was stirred for 20 mins at the same temperature. To a −10° C.-cooled suspension of L-leucine (131 mg) in acetone (4 ml), an aq. 0.5N sodium hydroxide solution (0.2 ml) was added dropwise. To the solution, the solution prepared above was added, removing deposited materials by filtration. The reaction solution was stirred for 30 mins at the same temperature. After addition of 1N hydrochloric acid (2 ml), the solution was extracted with ethyl acetate. The extract was washed with water and a saturated brine, successively, dried and then evaporated. The residue was purified by column chromatography on silica gel (EtOAc:EtOH=95:5) to give the title comound (255 mg) having the following physical data:

TLC: Rf 0.08 (EtOAc);

NMR: δ 6.20 (1H, m), 5.30–5.70 (2H, m), 4.64–4.79 (2H, m), 4.58 (1H, m), 3.74–4.30 (4H, m), 3.50 (2H, m), 0.80–1.01 (9H, m);

IR (liquid film method): 3300, 1720, 1640, 1525, 1435, 1360 cm$^{-1}$;

MS: m/z 463, 445, 392.

Reference Example 11(a)

Synthesis of N-[13E)-(11α,15α,17S)-6,9-dioxo-11,15-bis(tetrahydropyran-2-yloxy)-17,20-dimethylprost-13-en-1-oyl]-L-leucine

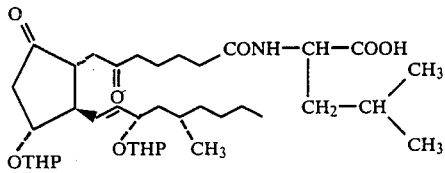

By the same procedure as reference example 11, using (13E)-(11α,15α,17S)-6,9-dioxo-11,15-bis(tetrahydropyran-2-yloxy)-17,20-dimethylprost-13-enoic acid (475 mg) and L-leucine (220 mg), the title compound (454 mg) having the following physical data was prepared:

TLC: Rf 0.10 (EtOAc:EtOH=95:5);

NMR: δ 6.15 (1H, m), 5.30–5.65 (2H, m), 4.65–4.80 (2H, m), 4.55 (1H, m), 3.95–4.28 (2H, m), 3.82 (2H, m), 3.54 (2H, m), 0.90–1.02 (12H, m);

IR (liquid film method): 3300, 1735, 1710, 1640, 1530, 1450, 1360, 1030, 1015, 970 cm$^{-1}$;

MS: m/z 491, 473.

Example 1

Synthesis of N-[(13E)-(11α,15α,16S,18S)-6,9-dioxo-11,15-dihydroxy-16,18-ethano-20-ethylprost-13-en-1-oyl]-L-phenylalanine (i.e. amide of 6-keto-16S,18S-ethano-20-ethyl-PGE$_1$ and L-phenylalanine)

A solution of the compound prepared in reference example 3 (108 mg) in 90% acetic acid (2.4 ml) was stirred at room temperature, and zinc dust (180 mg) was added to the solution with small portions. After confirmation by TLC, the mixture was filtered by cotton plug. The washings with a mixture of 90% acetic acid (5 ml), THF (0.5 ml) and water (1.5 ml) and the filtrate were combined and the mixture was stirred for 2 hrs at 60° C. After reaction, the reaction solution diluted with ethyl acetate was washed with water and a saturated brine, successively, dried and evaporated. To the residue, toluene was added and the mixture was evaporated azeotropically. The residue was purified by column chromatography on silica gel (EtOAc:CH$_3$OH=97:3) to give the title compound (26.5 mg) having the following physical data:

mp: 56°~60° C;

TLC: Rf 0.39 (CHCl$_3$:THF:AcOH=3:2:1);

NMR: δ 7.40–7.10 (5H, m), 6.4 (1H, d), 5.7–5.4 (2H, m), 4.9–4.7 (1H, m), 4.1 (1H, dd), 3.82 (1H, dd), 0.9 (3H, t);

IR (liquid film method): 3550–3150, 2910, 2850, 1740, 1710, 1640, 1525, 1075, 965 cm$^{-1}$;

MS: m/z 551, 533, 515, 489, 487, 276, 230, 120, 91.

Example 1(a)–1(e)

Following the procedure of example 1, using the appropriate compound prepared in reference example 3(a)–3(e), the compounds shown in the following table V were prepared.

TABLE V

| No. | Name & Structural formula | TLC | NMR | IR | MS |
|---|---|---|---|---|---|
| 1(a) | N—[(13E)-(11α,15α,16S,18S)—6,9-dioxo-11,15-dihydroxy-16,18-ethano-20-ethylprost-13-en-1-oyl]glycine i.e. amide of 6-keto-16S,18S—ethano-20-ethyl-PGE$_1$ and glycine | Rf 0.20 (CHCl$_3$: THF:AcOH = 3:2:1) | (CDCl$_3$ + CD$_3$OD): δ 5.7–5.35(2H,m), 4.06 (1H,dd), 3.9(2H,s), 3.76(1H,dd), 0.9(3H,t) | ν 3550–3150,2910, 2845,1740–1700, 1640,1530,1400, 1225,1070,970 | m/z 461,445, 443,425,368, 140,111 |
| 1(b) | N—[(13E)-(11α,15α,16S,18S)—6,9-dioxo-11,15-dihydroxy-16,18-ethano-20-ethylprost-13-en-1-oyl]-L-leucine i.e. amide of 6-keto-16S,18S—ethano-20-ethyl-PGE$_1$ and L-leucine | Rf 0.45 (CHCl$_3$: THF:AcOH = 3:2:1) | δ 6.35(1H,d), 5.75–5.45 (2H,m), 4.65–4.45(1H, m), 4.24–4.0(1H,m), 3.85(1H,dd), 1.05–0.8 (9H,m) | (CHCl$_3$ solution) ν 3550–2450,3420 2840,1730–1705, 1635,1520,1150, 1070,965 | m/z 517,499, 455,364,242, 214,196,86 |
| 1(c) | N—[(13E)-(11α,15α,16S,18S)—6,9-dioxo-11,15-dihydroxy-16,18-ethano-20-ethylprost-13-en-1-oyl]-L-proline i.e. amide of 6-keto-16S,18S—ethano-20-ethyl-PGE$_1$ and L-proline | Rf 0.16 (CHCl$_3$: THF:AcOH = 3:2:1) | δ 5.8–5.35(2H,m), 4.65–4.4(1H,m), 4.25–4.0(1H,m), 0.9(3H,t) | (CHCl$_3$ solution) ν 3650–2400,2925, 2855,1720,1620, 1440,1230,1080, 975,750 | m/z 501,483, 457,226 |
| 1(d) | N—[(13E)-(11α,15α,16S,18S)—6,9-dioxo-11,15-dihydroxy-16,18-ethano-20-ethylprost-13-en-1-oyl]-L-methionine i.e. amide of 6-keto-16S,18S—ethano-20-ethyl-PGE$_1$ and L-methionine | Rf 0.46 (CHCl$_3$: THF:AcOH = 3:2:1) | (CDCl$_3$ + CD$_3$OD): δ 5.7–5.35(1H,m), 4.60 (1H,m), 4.2–3.9(1H, m), 3.85–3.65(1H,m), 2.12(3H,s), 0.9(3H,t) | (CHCl$_3$ solution) ν 3600–2600,2925, 2860,1720,1640, 1230,1080,970, 750 | m/z 517,499, 469,386,368, 350,322,257 |

TABLE V-continued
| No. | Name & Structural formula | TLC | NMR | IR | MS |
|---|---|---|---|---|---|
| 1(e) | N—[(13E)-(11α,15α,16S,18S)—6,9-dioxo-11,15-dihydroxy-16,18-ethano-20-ethyl]prost-13-en-1-oyl]-D-leucine i.e. amide of 6-keto-16S,18S—ethano-20-ethyl-PGE₁ and D-leucine  | Rf 0.45 (CHCl₃: THF:AcOH = 3:2:1) | δ 6.38(1H,d), 5.8–5.4 (2H,m), 4.7–4.45(1H, m), 4.25–4.0(1H,m), 3.80(1H,dd), 1.0–0.8 (9H,m) | ν 3600–2500,2950, 1740,1705,1640, 1530,1270,1070, 970 | m/z 517,499, 455,364,242, 214,196,86 |

Example 2

Synthesis of N-[(13E)-(11α,15α,16S,18S)-6,9-dioxo-11,15-dihydroxy-16,18-ethano-20-ethylprost-13-en-1-oyl]-L-leucinol (i.e. amide of 6-keto-16S,18S-ethano-20-ethyl-PGE$_1$ and L-leucinol)

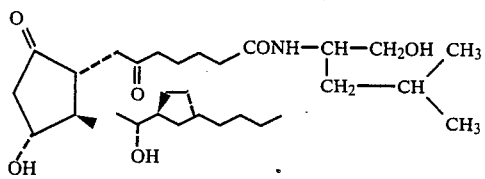

A mixture of the compound prepared in reference example 4 (200 mg), 65% acetic acid (3 ml) and THF (0.3 ml) was stirred for 3.5 hrs at 60° C. After cooling, the solution was diluted with ethyl acetate, the diluted solution was washed with water and a saturated brine, successively, dried and evaporated. The residue was purified by column chromatography on silica gel (EtOAc:CH$_3$OH=99:1) to give the title compound (45 mg) having the following physical data:

TLC: Rf 0.35 (CHCl$_3$:THF:AcOH=3:2:1);

NMR:δ 5.9–5.4 (3H, m), 4.25–3.95 (2H, m), 3.85 (1H, dd), 3.75–3.3 (3H, m), 1.0–0.75 (9H, m);

IR (liquid film method): 3600–2700, 2925, 2850, 1740, 1710, 1630, 1540, 1070, 970 cm$^{-1}$;

MS: m/z 503, 485, 472, 454, 378, 350.

Example 2(a)–2(d)

Following the procedure of example 2, using the appropriate compounds prepared in reference example 6, 10, 11 and 11(a), the compounds shown in the following table VI were prepared.

TABLE VI

| No. | Name & Structural formula | TLC | NMR | IR | MS |
|---|---|---|---|---|---|
| 2(a) | N—[(13E)-(11α,15α,17S)—6,9-dioxo-11,15-dihydroxy-17,20-dimethylprost-13-en-1-oyl]-L-phenylalanine methyl ester i.e. amide of 6-keto-17S,20-dimethyl-PGE$_1$ and L-phenylalanine methyl ester | Rf 0.16 (CHCl$_3$: THF:AcOH = 10:2:1) | δ 7.35–7.21(3H, m), 7.15–7.04 (2H,m), 6.10–5.95(1H,d), 5.74–5.50(2H, m), 4.96–4.82 (1H,m), 3.72 (3H,s), 3.22–3.00(2H,m), 0.96–0.82 (6H,m) | (liquid film) ν 3600–2300,1740 1710,1650,1530 1450,1430,1370, 1210,1080,970 | m/z 557, 539,521, 458,440, 412 |
| 2(b) | N—[(13E)-(11α,15α,17S)—6,9-dioxo-11,15-dihydroxy-17,20-dimethylprost-13-en-1-oyl]-glycine methyl ester i.e. amide of 6-keto-17S,20-dimethyl ester i.e. and glycine methyl ester | Rf 0.5 (CHCl$_3$: C$_2$H$_5$OH C$_2$H$_5$OH = 5:1) | δ 6.3–6.1(1H, m), 5.8–5.5(2H, m), 4.3–4.1(2H, m), 4.02(2H,d), 3.78(3H,s), 2.9–2.6(3H,m), 10–0.8(6H,m) | (liquid film) ν 3600–2300,1740 1710,1660,1540, 1370,1210,1080, 980 | m/z 467, 449,431, 368,350 |
| 2(c) | N—[(13E)-(11α,15α)-6,9-dioxo-11,15-dihydroxyprost-13-en-1-oyl[-L-leucine i.e. amide of 6-keto-PGE$_1$ and L-leucine | Rf 0.19 (EtOAc: HCOOH = 400:5) | δ 6.48(1H,d), 5.45–5.68(2H, m), 4.51(1H,m), 3.95–4.20(2H, m), 0.82–1.03 (9H,m) | (CHCl$_3$ solution) ν 3450,1735,1710, 1660,1500,1080, 970 | m/z 463, 445,242, 214,203, 196,173 159,149, 132,111, 107,105, 91,86 |
| 2(d) | N—[(13E)-(11α,15α,17S)—6,9-dioxo-11,15-dihydroxy-17,20-dimethylprost-13-en-1-oyl]-L-leucine i.e. amide of 6-keto-17S,20-dimethyl-PGE$_1$ and L-leucine | Rf 0.16 (EtOAc: HCOOH = 400:5) | δ 6.38(1H,d), 5.57(2H,m), 4.52(1H,m), 0.80–1.00(12H, m) | (CHCl$_3$ solution) ν 3400,1735,1710, 1660,1500,1080, 970 | m/z 491, 473,242, 214,186, 159,149, 147,133, 132,111, 105 |

Example 3

Synthesis of α-cyclodextrin clathrate of N-[(13E)-(11α,15α,16S,18S)-6,9-dioxo-11,15-dihydroxy-16,18-ethano-20-ethylprost-13-en-1-oyl]L-phenylalanine To a solution of N-[(13E)-(11α,15α,16S,18S)-6,9-dioxo-11,15-dihydroxy-16,18-ethano-20-ethylprost-13-en-1-oyl]-L-phenylalanine (3.51 g) dissolved in ethanol (3 ml), a solution of α-cyclodextrin (681 mg) in water (6 ml) was added. The mixture was stirred at room temperature and evaporated to give the title compound (705 mg).

The present invention includes within its scope pharmaceutical compositions which comprise a prostaglandin analogue of general formula I, or a cyclodextrin clathrate thereof, or a non-toxic salt thereof, in association with a pharmaceutical carrier or coating.

For use, in the treatment and/or prevention of diseases induced by cytodamage described above, the compounds of the present invention of general formula (I) or cyclodextrin clathrates thereof or non-toxic salts thereof will normally be administered systemically or partially, usually be oral or parenteral administration.

The dose to be administered is determined depending upon, for example, age, body weight, symptoms, the desired therapeutic effects, the route of administration, and the duration of the treatment.

In the human adult, for use in the treatment and/or the prevention of diseases induced by cytodamage, the doses per person per dose are generally between 0.1 and 500 µg, by oral administration, and between 0.01 and 50 µg, by parenteral administration, and can be administered up to several times per day.

As mentioned above, the doses to be used depend on various factors. Therefore, there may be cases in which doses greater than the ranges specified above, or lower than the ranges specified above, may be used.

Solid compositions included in the present invention for oral administration include compressed tablets, pills, dispersible powders and granules. In such solid composition, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethyl-cellulose phthalate-coated tablets or pills; two or more layers may be used. The compositions for oral administration also include capsules of absorbable material such as gelatin.

Liquid compositions included in the present invention for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions included in the present invention for oral administration include spray compositions which may be prepared by known methods and which comprise at least one compound of the present invention as active ingredient.

Compositions for parenteral administration by injection included in the present invention include sterile aqueous or nonaqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol and POLYSORBATE 80 (registered Trade Mark).

These compositions may also include adjuvants such as preserving, wetting, emulsifying, dispersing agents, stabilizers such as lactose, and dissolving adjuvants such as glutamic acid and aspertic acid. They may be sterilized, for example, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories and pessaries. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The following Examples illustrate pharmaceutical compositions according to the invention.

Example 4

Preparation of composition for injection

N-[(13E)-(11α,15α,16S,18S)-6,9-dioxo-11,15-dihydroxy-16,18-ethano-20-ethylprost-13-en-1-oyl]-L-leucine (2 mg), and maltose (6 g) were dissolved in distilled water for injection (40 ml). The solution was sterilized in conventional manner, placed in 0.4 ml portions in 5 ml ampoules and freeze dried to obtain 100 ampoules each containing 20 µg of the active ingredient.

Example 5

Preparation of soft capsule

A solution of N-[(13E)-(11α,15α,16S,18S)-6,9-dioxo-11,15-dihydroxy-16,18-ethano-20-ethylprost-13-en-1-oyl]-L-leucine (30 mg) in chloroform (10 ml) was added to MCT (100 ml; middle chain triglyceride) and the mixture was mixed well. After removing chloroform under reduced pressure, the residue was machine filled into 100 soft capsules to give capsules each containing 30 µg of the active ingredient.

We claim:

1. A 6-keto-prostaglandin $E_1$ derivative of the general formula:

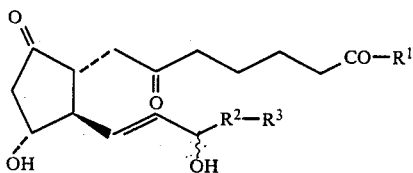

(wherein R¹ represents an amino acid or amino alcohol residue attached to the CO-group by its amino group and selected from the group consisting of glycine, alanine, valine, isoleucine, leucine, serine, threonine, proline, asparagine, glutamine, methionine, phenylalanine, tyrosine, aspartic acid, glutamic acid and alkyl esters thereof of from 1 to 8 carbon atoms in the esterifying alkyl group and the corresponding amino alcohols in which the carboxy groups are replaced by hydroxymethyl groups, R² represents a single bond or an alkylene group of from 1 to 4 carbon atoms, R³ represents (i) an alkyl group of from 1 to 8 carbon atoms, (ii) a cycloalkyl group of from 4 to 7 carbon atoms, which is unsubstituted or substituted by at least one alkyl group of from 1 to 8 carbon atoms or (iii) a phenyl or phenoxy group, which is unsubstituted or substituted by at least one chlorine atom, trifluoromethyl group or alkyl group of from 1 to 3 carbon atoms with the proviso that when R² represents a single bond R³ does not represent a phenoxy group) or a cyclodextrin clathrate thereof or a salt thereof.

2. A compound according to claim 1 wherein the hydroxy group attached to the 15-position carbon atom is in α-configuration.

3. A compound according to claim 1, wherein R³ represents an alkyl group of from 1 to 8 carbon atoms.

4. A compound according to claim 3, which is
N-[(13E)-(11α,15α,17S)-6,9-dioxo-11,15-dihydroxy-17,20-dimethylprost-13-en-1-oyl]glycine methyl ester,
N-[(13E)-(11α,15α,17S)-6,9-dioxo-11,15-dihydroxy-17,20-dimethylprost-13-en-1-oyl]-L-phenylalanine methyl ester,
N-[(13E)-(11α,15α)-6,9-dioxo-11,15-dihydroxyprost-13-en-1-oyl]-L-leucine or
N-[(13E)-(11α,15α,17S)-6,9-dioxo-11,15-dihydroxy-17,20-dimethylprost-13-en-1-oyl]-L-leucine.

5. A compound according to claim 1, wherein R³ is a cycloalkyl group of from 4 to 7 carbon atoms optionally substituted by an alkyl group of from 1 to 8 carbon atoms.

6. A compound according to claim 5, which is
N-[(13E)-(11α,15α,16S,18S)-6,9-dioxo-11,15-dihydroxy-16,18-ethano-20-ethylprost-13-en-1-oyl]-L-phenylalanine,
N-[(13E)-(11α,15α,16S,18S)-6,9-dioxo-11,15-dihydroxy-16,18-ethano-20-ethylprost-13-en-1-oyl]glycine,
N-[(13E)-(11α,15α,16S,18S)-6,9-dioxo-11,15-dihydroxy-16,18-ethano-20-ethylprost-13-en-1-oyl]-L-leucine,
N-[(13E)-(11α,15α,16S,18S)-6,9-dioxo-11,15-dihydroxy-16,18-ethano-20-ethylprost-13-en-1-oyl]-L-proline,
N-[(13E)-(11α,15α,16S,18S)-6,9-dioxo-11,15-dihydroxy-16,18-ethano-20-ethylprost-13-en-1-oyl]-L-methionine,
N-[(13E)-(11α,15α,16S,18S)-6,9-dioxo-11,15-dihydroxy-16,18-ethano-20-ethylprost-13-en-1-oyl]-D-leucine or
N-[(13E)-(11α,15α,16S,18S)-6,9-dioxo-11,15-dihydroxy-16,18-ethano-20-ethylprost-13-en-1-oyl]-L-leucinol.

7. A pharmaceutical composition useful in the prevention or treatment of cytodamage in a mammalian host which comprises, as active ingredient, an effective amount of a 6-keto-prostaglandin E₁ derivative of the general formula (I) depicted in claim 1 wherein the various symbols are as defined in claim 1, or a cyclodextrin clathrate thereof, or a non-toxic salt thereof, in association with a pharmaceutical carrier or coating.

8. A method for the prevention or treatment of cytodamage in a mammalian host which comprises administering to a host subject to, or suffering from, cytodamage an effective amount of a 6-keto-prostaglandin E₁ derivative of general formula I depicted in claim 1 or a non-toxic salt thereof or a cyclodextrin clathrate thereof.

9. A compound of the general formula:

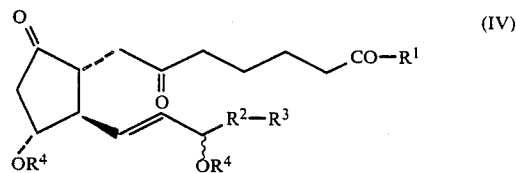

(IV)

wherein R⁴ represents a tetrahydropyran-2-yl, tetrahydrofuran-2-yl or 1-ethoxyethyl group and the other symbols are as defined in claim 1.

10. A compound of the general formula:

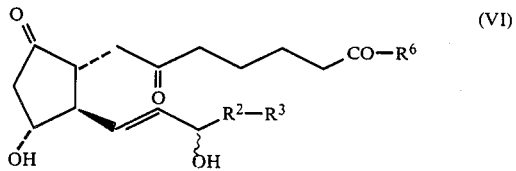

(VI)

wherein R⁶ represents an amino acid residue as defined for R₁ in which the carboxy group is protected by a trihaloethyl group and the other symbols are as defined in claim 1.

* * * * *